(12) United States Patent
Shao et al.

(10) Patent No.: US 9,738,575 B2
(45) Date of Patent: Aug. 22, 2017

(54) APPARATUS FOR PRODUCING ETHYLENE AND A PRODUCING METHOD THEREOF

(71) Applicants: CHINA PETROLEUM & CHEMICAL CORPORATION, Beijing (CN); Shanghai Research Institute of Petrochemical Technology SINOPEC, Shanghai (CN)

(72) Inventors: Baixiang Shao, Shanghai (CN); Wei Shen, Shanghai (CN); Zhi He, Shanghai (CN); Yiming Wu, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY SINOPEC, Shanghai (CN)

( * ) Notice: Subject to any disclaimer, the term of this patent is extended or adjusted under 35 U.S.C. 154(b) by 300 days.

(21) Appl. No.: 14/397,967

(22) PCT Filed: May 15, 2013

(86) PCT No.: PCT/CN2013/075653
§ 371 (c)(1),
(2) Date: Oct. 30, 2014

(87) PCT Pub. No.: WO2013/170752
PCT Pub. Date: Nov. 21, 2013

(65) Prior Publication Data
US 2015/0133708 A1 May 14, 2015

(30) Foreign Application Priority Data

May 16, 2012 (CN) .......................... 2012 1 0150227
Jul. 12, 2012 (CN) .......................... 2012 1 0239790
Jul. 12, 2012 (CN) .......................... 2012 1 0239797

(51) Int. Cl.
C07C 1/24 (2006.01)
C07C 7/00 (2006.01)
C07C 7/09 (2006.01)

(52) U.S. Cl.
CPC ................ *C07C 7/005* (2013.01); *C07C 1/24* (2013.01); *C07C 7/09* (2013.01); *C07C 2521/04* (2013.01); *C10G 2400/20* (2013.01)

(58) Field of Classification Search
CPC ....... C07C 1/24; C07C 11/04; C07C 2521/04; C07C 7/005; C07C 7/09; C10G 2400/20
See application file for complete search history.

(56) References Cited

U.S. PATENT DOCUMENTS 4,134,926 A  1/1979 Tsao et al.
4,232,179 A  11/1980 Valladares Barrocas et al.
(Continued)

FOREIGN PATENT DOCUMENTS

CN  101244970 A  8/2008
CN  101306973 A  11/2008
(Continued)

OTHER PUBLICATIONS

Search Report issued Jun. 6, 2014, by the Chinese Patent Office in Chinese Application No. 201210239797.1. (2 pages).
(Continued)

*Primary Examiner* — Sharon Pregler
(74) *Attorney, Agent, or Firm* — Buchanan Ingersoll & Rooney PC

(57) ABSTRACT

An apparatus for producing ethylene includes: a reactor; a first separation column, connected to the reactor; a second separation column, the upper part of the second separation column being connected to the bottom of the first separation
(Continued)

column, and the top of the second separation column being connected to the lower part of the first separation column; a first condenser, an inlet of the first condenser being connected to the top of the first separation column, and an outlet of the first condenser being connected to the upper part of the first separation column; and a third separation column, used for receiving a second part of a first condensate from the condenser and separating the received part. A method for producing ethylene using the aforementioned apparatus is also described.

20 Claims, 3 Drawing Sheets

(56) References Cited

U.S. PATENT DOCUMENTS

| | | | |
|---|---|---|---|
| 4,396,789 | A | 8/1983 | Barrocas et al. |
| 2008/0156692 | A1 | 7/2008 | De Rezende Pinho et al. |
| 2009/0082605 | A1 | 3/2009 | Bailey et al. |
| 2011/0105815 | A1 | 5/2011 | Minoux et al. |
| 2012/0220796 | A1* | 8/2012 | Lefenfeld ............... C07C 1/24 560/129 |

FOREIGN PATENT DOCUMENTS

| | | |
|---|---|---|
| CN | 101336218 A | 12/2008 |
| CN | 101376551 A | 3/2009 |
| CN | 101306973 B | 9/2011 |
| CN | 202081036 U | 12/2011 |
| CN | 102372558 A | 3/2012 |
| CN | 102372567 A | 3/2012 |
| JP | 2003-236528 A | 8/2003 |
| WO | WO 2009/098269 A1 | 8/2009 |
| WO | WO 2011/037681 A1 | 3/2011 |

OTHER PUBLICATIONS

Search Report issued Aug. 14, 2014, by the Chinese Patent Office in Chinese Application No. 201210239790.X. (2 pages).

Search Report issued Aug. 18, 2014, by the Chinese Patent Office in Chinese Application No. 201210150227.5. (2 pages).

International Search Report (PCT/ISA/210) mailed on Aug. 8, 2013, by State Intellectual Property Office of the P.R. China as the International Searching Authority for International Application No. PCT/CN2013/075653.

* cited by examiner

APPARATUS FOR PRODUCING ETHYLENE AND A PRODUCING METHOD THEREOF

CROSS REFERENCE TO RELATED APPLICATION

The present application claims the priorities of Chinese patent application CN 201210150227.5, filed on May 16, 2012, and CN 201210239790.X and CN 201210239797.1, both filed on Jul. 12, 2012, the entire content and disclosures of which are incorporated herein by reference.

FIELD OF THE INVENTION

The present disclosure relates to an apparatus for producing ethylene and a producing method thereof, particularly to an apparatus for producing ethylene through ethanol dehydration and a producing method thereof.

BACKGROUND OF THE INVENTION

Ethylene is an important basic bulk raw material in organic chemical industry, which is mainly used for producing polyethylene, polyvinyl chloride, ethylene oxide/ethylene glycol, ethylbenzene/styrene, vinyl acetate and other kinds of organic chemical products. Currently, ethylene is mainly produced through catalytic cracking method using petroleum as raw material at home and abroad. In recent years, the research on the production of ethylene using non-petroleum raw material has produced new breakthroughs, especially the technology of producing ethylene through ethanol dehydration. In this technology, bio-derived ethanol is used as raw material, so that the dependence on petroleum resources is avoided. For oil-poor countries and regions, as well as for countries and regions with agriculture as the main industry, the raw material for producing ethanol can be obtained easily and is reliable, which lays a solid raw material foundation for the production of ethylene, and the problems of fossil resources shortage and severe environmental pollution can be solved. Especially, with the rapid development of bio-technology, the technology of producing ethanol with biological methods has been improving continuously. The sources of raw material for producing ethanol are becoming more and more various, and the cost of raw material is becoming more reasonable, therefore, the technology of producing ethylene through ethanol dehydration is gaining more and more attentions.

It is important to develop a new technology with good economic benefits and strong market competitiveness for producing ethylene with ethanol, aiming at improving the technological process, reducing unit ethanol consumption and improving the efficiency of the apparatus.

There are many methods for producing ethylene through ethanol dehydration in documents and patents already disclosed at home and abroad, and the basic process thereof mainly comprises fixed-bed process and fluidized-bed process. It is raised by ABB Lummu in late 1970s to produce ethylene through ethanol dehydration with a fluidized-bed technology (U.S. Pat. No. 4,134,926), however, the technology has not been put into industrial applications. The fixed-bed process is mainly used in the present industrial applications, comprising isothermal fixed-bed process and adiabatic fixed-bed process.

Initially, ethanol dehydration reaction is conducted in tubular fixed-bed, the reaction pressure thereof is normal pressure, and the reaction heat is provided to the reaction by direct heating or indirect heating through heating medium (such as molten-salt). During the reaction process, the reaction temperature and the material flow speed are key factors. On the one hand, if the reaction temperature is too high or the material flow speed is too low, other by-products would be produced. On the other hand, if the material flow speed is increased, the conversion rate of ethanol would decrease. To solve the aforesaid problem, US patent (U.S. Pat. No. 4,232,179) raised the adiabatic process of ethanol dehydration reaction, i.e., ethanol dehydration reaction is conducted in adiabatic fixed-bed. The reaction material is heated to the required temperature before entering into the reactor, to ensure normal reaction. After that, a reaction technology of three-stage adiabatic fixed-bed (U.S. Pat. No. 4,396,789) is raised, and a ethylene production apparatus with a production capacity of 60 thousand tons per year is constructed using the aforesaid technology in the earlier 1980s. Three adiabatic fixed-bed reactors are connected in series in the technology, the mixed feedstock of ethanol and steam in each of the inlets of the reactors is pre-heated by one furnace, and the unreacted ethanol, ethyl ether and other by-products are recycled. The addition of steam reduces coking during reaction process, the lifetime of the catalyst is prolonged, and the yield of ethylene is improved. The operating data of the apparatus showed that, when the temperature of the inlet of the reactor is 450° C., the conversion rate of ethanol reaches 98%, and the regeneration period of the catalyst is at least one year. In addition, Halcon/SD Company developed a dual-mode technology of adiabatic or isothermal fixed-bed in the 1970s, wherein the isothermal fixed-bed technology was put into industrial application. The operating data of the apparatus showed that, under the conditions of the reaction temperature being 318° C. and the LHSV being 0.23 hour$^{-1}$, the selectivity of ethylene is 96.8% (by molar), the conversion rate of ethanol is 99.1%, and the regeneration period of the catalyst is 8 months. After that, Halcon/SD Company developed the reaction technology of multi-stage adiabatic fixed-bed, i.e., ethanol, after being diluted in water steam, enters into the multi-stage adiabatic fixed-bed to produce ethylene through ethanol dehydration reaction; polymer grade ethylene product is obtained after the reaction gas is washed, compressed, alkaline cleaned, dried and cryogenic rectified. The test data showed that, under the conditions of the reaction temperature being 465° C., the LHSV being 0.8 hour$^{-1}$, and the ratio of water steam and ethanol being 3:1, the selectivity of ethylene is 99.4% (by molar), the conversion rate of ethanol is 99.9%, and the regeneration period of the catalyst is 8 months. Lummus Company realized the industrialization of fixed-bed technology as early as 1960s. The tubular isothermal reactor was used in the technology, and the heat needed during the reaction process is provided by a hot oil system. The regeneration period of silica-alumina catalyst is 3 weeks, and it needs 3 days to regenerate the catalyst once. Under the conditions of the reaction temperature being 315° C. and the reaction pressure being 0.16 MPa, the selectivity of ethylene is 94% (by molar), and the conversion rate of ethanol is 99%.

The products separation technology and how to improve the yield of ethylene during the process of producing ethylene through ethanol dehydration are relatively less referred to in the prior documents or reports, especially the technical problem of recycling ethylene in light components streams and heavy components materials. Two-column process is mainly used in the prior separation technology, in which the unrefined ethylene enters into the ethylene fractionating column first, after the light components are condensed at the top of said column, the vapor-phase components are exhausted, the liquid-phase components are fed to the light components stripper, whereby the light components are removed from the liquid-phase components, and the refined ethylene with the purity of 99.99% is obtained. Although the refined ethylene with the purity of 99.99% is obtained by the aforesaid technology, since the stripper is used to remove the light components, and ethylene in the heavy components materials is not recycled, there is the problem of ethylene loss in the aforesaid technology. The patent (ZL200710040705.64) raised an adiabatic flash method to recycle ethylene from the liquid at the bottom of the ethylene fractionating column. Although ethylene is partly recycled with the aforesaid method, the recycling efficiency thereof is relatively low. The present disclosure provides a new separating and refining method for producing ethylene through bio-derived ethanol dehydration, with the advantages of high ethylene recycling efficiency, low power consumption and good product quality.

In addition, the processing technology of organic wastewater in producing ethylene through ethanol dehydration is relatively less referred to in the prior documents or reports, especially how to reduce the consumption of the raw material, i.e., ethanol, and the technical problem of resource utilization of organic wastewater. Currently, the organic wastewater of industrial apparatus directly enters into the wastewater treatment equipment out of said apparatus without being treated. Consequently, on the one hand, the organic substances, especially ethanol in the organic wastewater are not utilized, and the consumption of ethanol increases; on the other hand, the concentration of organic substances in wastewater is relatively high, as a result, the wastewater treatment difficulty and treatment cost of wastewater treatment equipment out of said apparatus increase inevitably. The patent (CN101376551B) raised a treatment method for treating organic wastewater during the production of ethylene through ethanol dehydration with a four-unit process, but there are the disadvantages of complicated technology, long process and high investment in the aforesaid method.

SUMMARY OF THE INVENTION

The purpose of the present disclosure is to solve the problems of low ethylene yield, the organic wastewater generated during the producing process being not treated sufficiently, or being treated but with the disadvantages of complicated technology, long process and high investment as aforementioned in the prior art. The present disclosure provides a new apparatus for producing ethylene and a producing method thereof, whereby ethylene can be produced in a high yield and low power consumption way, and the organic wastewater generated therein can be treated with simple technology, short process and low investment.

The present disclosure provides an apparatus for producing ethylene, comprising:

a reactor, used for dehydrating ethanol and obtaining a ethylene stream including ethane, ethanol, ethyl ether and by-products containing three or more carbon atoms;

a first separation column, connected to said reactor, used for separating said ethylene stream including ethane, ethanol, ethyl ether and by-products containing three or more carbon atoms from said reactor to obtain a first light components containing ethylene at the top of said first separation column and a first heavy components containing ethylene at the bottom of said first separation column;

a second separation column, the upper part of said second separation column being connected to the bottom of said first separation column, the top of said second separation column being connected to the lower part of said first separation column, said second separation column used for receiving and separating the first heavy components containing ethylene from the bottom of said first separation column to obtain a second light components containing ethylene at the top of said second separation column and a second heavy components at the bottom of said second separation column, wherein the second light components are returned to the lower part of said first separation column and the second heavy components are exhausted;

a first condenser, an inlet of said first condenser being connected to the top of said first separation column, and an outlet of said first condenser being connected to the upper part of said first separation column, said first condenser used for condensing the first light components containing ethylene from the top of said first separation column to obtain a first condensate, and a first part of said first condensate is returned to the upper part of said first separation column; and a third separation column, used for receiving and separating a second part of said first condensate from said first condenser to obtain a liquid ethylene at the bottom of said third separation column and a third light components at the top of said third separation column.

In one preferred embodiment of the apparatus for producing ethylene, said apparatus further comprises:

a second condenser, connected to the top of said third separation column, used for receiving and condensing the third light components from the top of said third separation column to obtain a second condensate; and a first reflux tank, connected to said second condenser and said third separation column respectively, used for receiving a second condensate from said second condenser and returning said second condensate to the upper part of said third separation column.

In one embodiment of the apparatus for producing ethylene, said reactor and said first separation column can be connected in a variety of conventional methods, including connected directly and connected through a dryer or a condenser, to process said ethylene stream into a stream suitable for serving as the feedstock of said first separation column.

In one preferred embodiment of the apparatus for producing ethylene, said apparatus further comprises:

a quenching column, connected between said reactor and said first separation column, used for receiving and water quenching the ethylene stream including ethane, ethanol, ethyl ether and by-products containing three or more carbon atoms from said reactor to obtain a quenched ethylene stream at the top of said quenching column and organic wastewater including ethane, ethanol, ethyl ether and by-products containing three or more carbon atoms at the bottom of said quenching column, wherein the quenched ethylene stream is fed to said first separation column; and a fourth separation column, connected to the bottom of said quenching column, used for receiving and separating the organic wastewater including ethane, ethanol, ethyl ether and by-products containing three or more carbon atoms from the bottom of said quenching column to obtain a water stream at the bottom of said fourth separation column and a fourth light components including ethane, ethanol, ethyl ether and by-products containing three or more carbon atoms at the top of said fourth separation column.

In one preferred embodiment of the apparatus for producing ethylene, said apparatus further comprises:

a third condenser, connected to the top of said fourth separation column, used for receiving and condensing a fourth light components from the top of said fourth separation column to obtain a third condensate; and a second reflux tank, connected to said third condenser and said fourth separation column respectively, used for receiving a third condensate from said third condenser, wherein a first part of said third condensate is returned to the upper part of said fourth separation column, and a second part of said third condensate is exhausted.

In one preferred embodiment of the apparatus for producing ethylene, the operating temperature of said first separation column ranges from −35° C. to 30° C., the operating pressure thereof ranges from 1.3 MPaG to 4.5 MPaG, and the theoretical plate number thereof ranges from 50 to 140.

In one preferred embodiment of the apparatus for producing ethylene, the operating temperature of said second separation column ranges from −15° C. to 80° C., the operating pressure thereof ranges from 1.0 MPaG to 4.0 MPaG, and the theoretical plate number thereof ranges from 2 to 50.

In one preferred embodiment of the apparatus for producing ethylene, the operating temperature of said third separation column ranges from −45° C. to −10° C., the operating pressure thereof ranges from 1.2 MPaG to 4.3 MPaG, and the theoretical plate number thereof ranges from 2 to 60.

In one preferred embodiment of the apparatus for producing ethylene, the operating temperature of said fourth separation column ranges from 30° C. to 210° C., the operating pressure thereof ranges from 0 MPaG to 1.0 MPaG, and the theoretical plate number thereof ranges from 2 to 98.

In the apparatus of the present disclosure, said first separation column and said third separation column are preferably selected as fractionating column, and said second separation column and said fourth separation column are preferably selected as stripper.

The present disclosure further provides a method for producing ethylene using the aforementioned apparatus, comprising:

1) feeding ethanol to the reactor to dehydrate said ethanol to obtain an ethylene stream including ethane, ethanol, ethyl ether and by-products containing three or more carbon atoms;

2) feeding said ethylene stream including ethane, ethanol, ethyl ether and by-products containing three or more carbon atoms obtained in step 1) to said first separation column and separating the ethylene stream to obtain a first light components containing ethylene at the top of said first separation column and a first heavy components containing ethylene at the bottom of said first separation column;

3) feeding the first heavy components containing ethylene obtained in step 2) to the upper part of said second separation column, and separating the first heavy components in said second separation column to obtain a second light components containing ethylene at the top of said second separation column and a second heavy components at the bottom of said second separation column, wherein the second light components are returned to the lower part of said first separation column and the second heavy components are exhausted; at the same time, feeding the first light components containing ethylene obtained in step 2) to said first condenser to obtain a first condensate, wherein the first part of the first condensate is returned to the upper part of said first separation column; and 4) feeding the second part of said first condensate to a third separation column to obtain a liquid ethylene at the bottom of said third separation column and a third light components at the top of said third separation column.

In one preferred embodiment of the method for producing ethylene, said method further comprises:

5) feeding said third light components obtained in step 4) to a second condenser to obtain a second condensate; and 6) feeding said second condensate obtained in step 5) to a first reflux tank, and then the second condensate is returned to the upper part of said third separation column through said first reflux tank.

In one preferred embodiment of the method for producing ethylene, said method further comprises:

before feeding the ethylene stream including ethane, ethanol, ethyl ether and by-products containing three or more carbon atoms obtained in step 1) to said first separation column in step 2), feeding aforementioned ethylene stream to a quenching column first and water quenching aforementioned ethylene stream, and then feeding the quenched ethylene stream obtained at the top of said quenching column to said first separation column to obtain an organic wastewater including ethane, ethanol, ethyl ether and by-products containing three or more carbon atoms at the bottom of said quenching column; the organic wastewater is then fed to a fourth separation column to obtain a water stream with organic contents less than 20 ppm by volume at the bottom of said fourth separation column and a fourth light components including ethane, ethanol, ethyl ether and by-products containing three or more carbon atoms at the top of said fourth separation column.

In one preferred embodiment of the method for producing ethylene, said method further comprises:

feeding the fourth light components to a third condenser to obtain a third condensate; and then the third condensate is fed to a second reflux tank, wherein a first part of said third condensate is returned to the upper part of said fourth separation column through said second reflux tank and a second part of said third condensate is exhausted.

In one preferred embodiment of the method for producing ethylene, the operating temperature of said first separation column ranges from −35° C. to 30° C., the operating pressure thereof ranges from 1.3 MPaG to 4.5 MPaG, and the theoretical plate number thereof ranges from 50 to 140.

In one preferred embodiment of the method for producing ethylene, the operating temperature of said second separation column ranges from −15° C. to 80° C., the operating pressure thereof ranges from 1.0 MPaG to 4.0 MPaG, and the theoretical plate number thereof ranges from 2 to 50.

In one preferred embodiment of the method for producing ethylene, the operating temperature of said third separation column ranges from −45° C. to −10° C., the operating pressure thereof ranges from 1.2 MPaG to 4.3 MPaG, and the theoretical plate number thereof ranges from 2 to 60.

In one preferred embodiment of the method for producing ethylene, the operating temperature of said third separation column ranges from 30° C. to 210° C., the operating pressure thereof ranges from 0 MPaG to 1.0 MPaG, and the theoretical plate number thereof ranges from 2 to 98.

In one preferred embodiment of the method for producing ethylene, the weight ratio of the first part of said first condensate and the second part of said first condensate ranges from 1 to 6:1.

In one preferred embodiment of the method for producing ethylene, the weight ratio of the first part of said third condensate and the second part of said third condensate ranges from 0.1 to 6:1.

In the method of the present disclosure, the catalyst in the reactor is one or more selecting from a group consisting of γ-Al$_2$O$_3$, ZSM molecular sieve, β molecular sieve and mordenite. Other catalyst and the combination of multiple catalysts can also be used therein according to actual needs.

The beneficial effects achieved by the present disclosure are:

1) Be means of the apparatus and method of the present invention, the defect of inadequate ethylene recycling in the prior art can be overcome, the yield of ethylene is increased, and the power consumption is reduced; besides, the operation is more convenient. It is proved by tests that, by means of the technical solution of the present disclosure, the power consumption of unrefined ethylene separation reduces by 13.25%, the amount of ethylene left in heavy components reduces from 22% to 3%, the purity and yield of ethylene product are further improved, and a good technical effect is achieved.

2) Be means of the apparatus and method of the present invention, ethanol, ethyl ether, a small amount of ethylene, and hydrocarbon containing three or more carbon atoms are removed from the organic wastewater, so that the organic substances in organic wastewater, especially ethanol get resource utilization, and the consumption of raw material, i.e., ethanol is reduced; at the same time, after being treated by the technology of the present disclosure, the depleted organic wastewater contains only a very small amount of organic substances, as a result, the treatment of the wastewater treatment equipment out of the apparatus is easier, and the treatment cost thereof is reduced. The technical solution of the present disclosure has the advantages of simple technology, short process and low investment. It is proved by tests that, for an apparatus with an annual capacity of ten thousand tons level, 222 tons of unrefined ethanol can be recycled from organic wastewater per year (the concentration is about 80% wt), the concentration of organic substances in organic wastewater is reduced from 0.265% to less than 20 ppm, and a good technical effect is achieved.

THE REFERENCE SIGNS

1—ethylene stream including ethane, ethanol, ethyl ether and by-products containing three or more carbon atoms
2—the first heavy components containing ethylene
3—the first light components containing ethylene
4—the second light components containing ethylene
5—the liquid ethylene
6—the first part of the first condensate
7—the second part of the first condensate
8—the third light components
9—the first vapor-phase stream
10—the second condensate
11—the second heavy components
12—ethanol stream
13—the gas stream of the reaction products
14—cooling water
15—quenched ethylene stream
16—organic wastewater
17—water stream
19—the fourth light components
20—the third condensate
21—the first part of the third condensate
22—the second part of the third condensate
23—the second vapor-phase stream;
24—the first separation column
25—the first condenser
26—the third separation column
27—the second separation column
28—the reactor
29—the second condenser
30—the first reflux tank
31—the quenching column
32—the fourth separation column
33—the third condenser
34—the second reflux tank

DETAILED DESCRIPTION OF THE EMBODIMENTS

The present disclosure will be explained in details with reference to the embodiments and the accompanying drawings, but the protection scope of the present disclosure is not limited by the following embodiments. It is important to note that as long as there is no structural conflict, all the technical features mentioned in all the embodiments may be combined together in any manner, and the technical solutions obtained in this manner all fall within the scope of the present disclosure.

EXAMPLE 1

Figure 1:
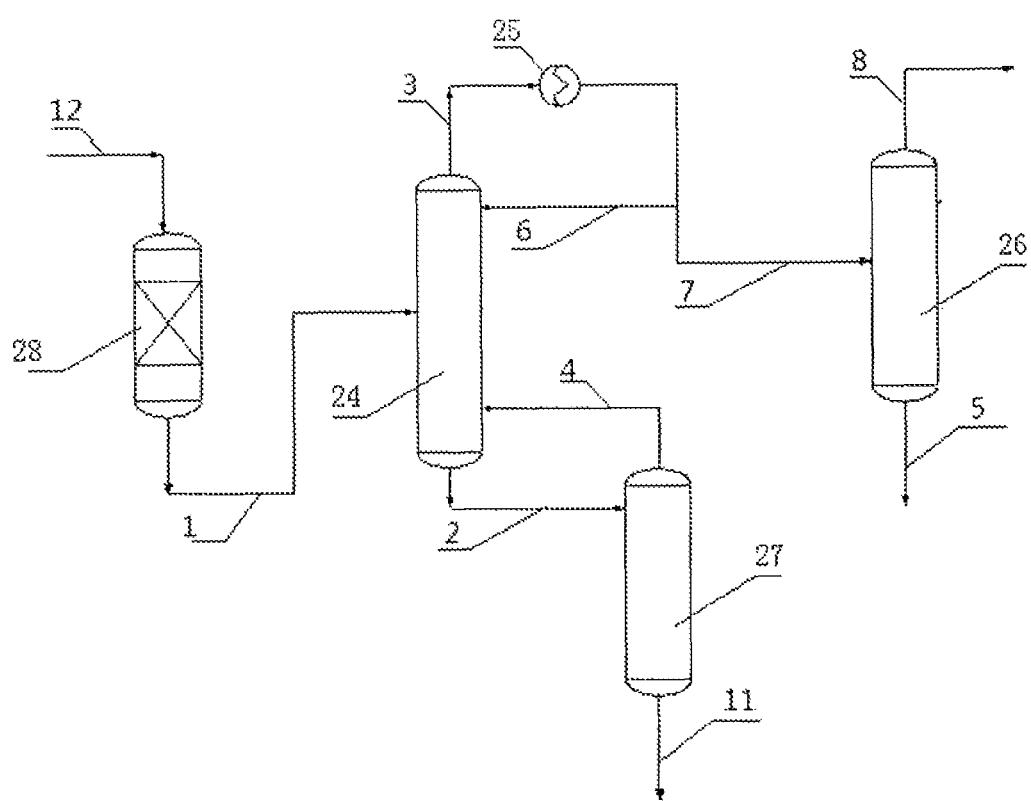
FIG. 1 is a schematic diagram of one specific embodiment of the apparatus of the present disclosure.

As shown in FIG. 1, the apparatus of the present embodiment comprises:

a reactor 28, used for dehydrating ethanol and obtaining a ethylene stream 1 including ethane, ethanol, ethyl ether and by-products containing three or more carbon atoms;

a first separation column 24, connected to said reactor 28, used for separating said ethylene stream 1 including ethane, ethanol, ethyl ether and by-products containing three or more carbon atoms from said reactor 28 to obtain a first light components 3 containing ethylene at the top of said first separation column 24 and a first heavy components 2 containing ethylene at the bottom of said first separation column 24;

a second separation column 27, the upper part of said second separation column 27 being connected to the bottom of said first separation column 24, the top of said second separation column 27 being connected to the lower part of said first separation column 24, said second separation column 27 used for receiving and separating the first heavy components 3 containing ethylene from the bottom of said first separation column 24 to obtain a second light components 4 containing ethylene at the top of said second separation column 27 and a second heavy components 11 at the bottom of said second separation column 27, wherein the second light components 4 are returned to the lower part of said first separation column and the second heavy components 11 are exhausted;

a first condenser 25, an inlet of said first condenser 25 being connected to the top of said first separation column 24, and an outlet of said first condenser 25 being connected to the upper part of said first separation column 24, said first condenser 25 used for condensing the first light components 3 containing ethylene from the top of said first separation column 24 to obtain a first condensate, and a first part 6 of said first condensate is returned to the upper part of said first separation column 24; and a third separation column 26, used for receiving and separating a second part 7 of said first condensate from said first condenser 25 to obtain a liquid ethylene 5 at the bottom of said third separation column 26 and a third light components 8 at the top of said third separation column 26.

EXAMPLE 2

Figure 2:
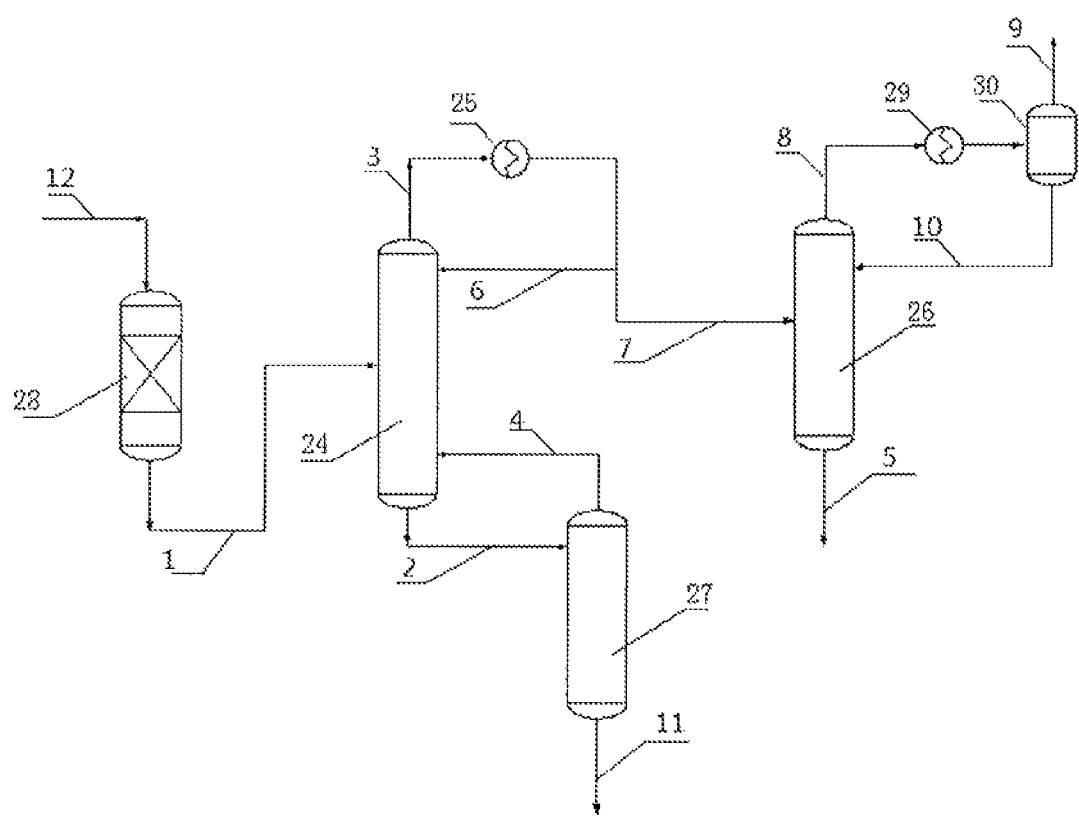
FIG. 2 is a schematic diagram of another specific embodiment of the apparatus of the present disclosure.

As shown in FIG. 2, the apparatus of embodiment 1 further comprises:

a second condenser 29, connected to the top of said third separation column 26, used for receiving and condensing the third light components 8 from the top of said third separation column 26 to obtain a second condensate 10; and a first reflux tank 30, connected to said second condenser 29 and said third separation column 26 respectively, used for receiving a second condensate 10 and a first vapor-phase stream 9 from said second condenser 29, wherein the second condensate 10 is returned to the upper part of said third separation column 26, and the first vapor-phase stream 9 is exhausted.

EXAMPLE 3

Figure 3:
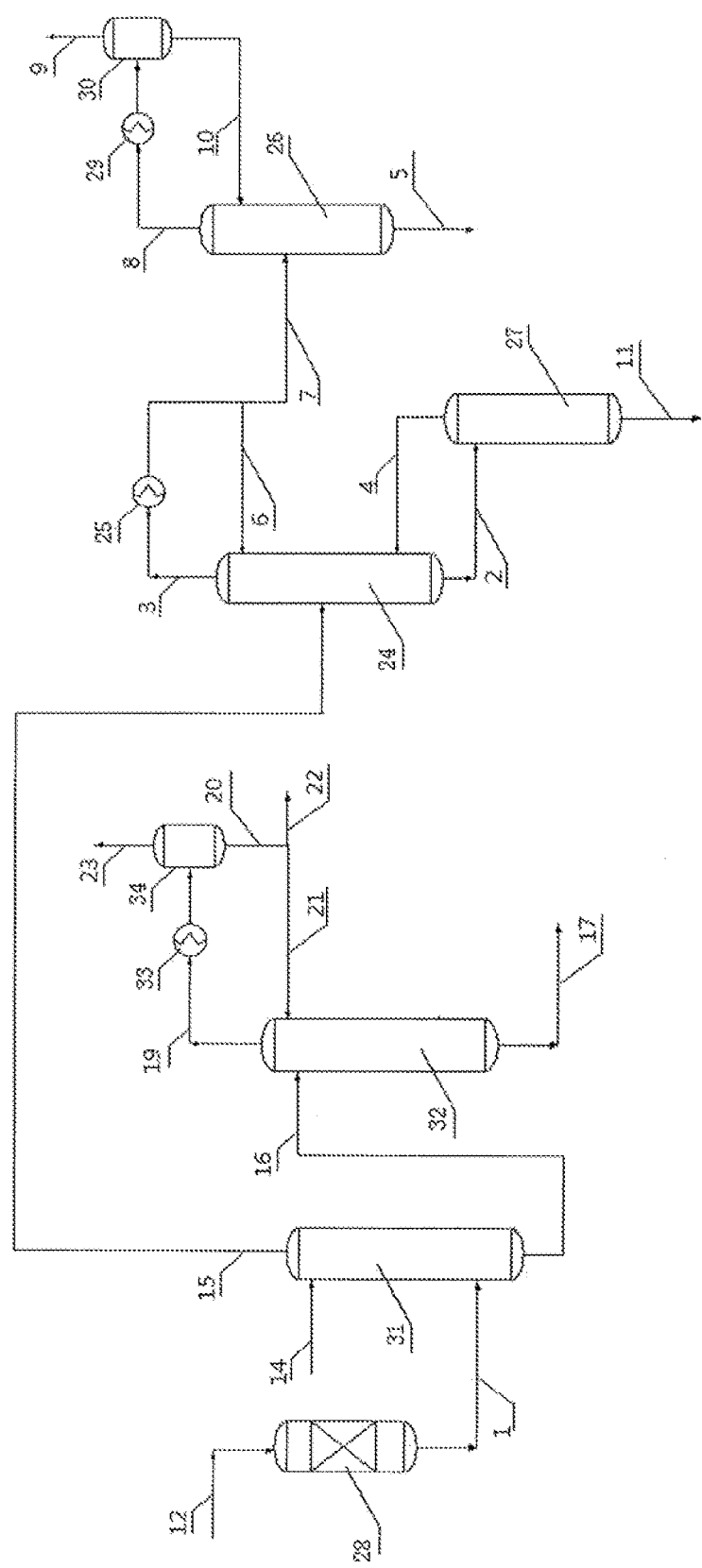
FIG. 3 is a schematic diagram of another specific embodiment of the apparatus of the present disclosure.

As shown in FIG. 3, on the basis of embodiment 2, the apparatus further comprises:

a quenching column 31, connected between said reactor 28 and said first separation column 24, used for receiving and water quenching the ethylene stream 1 including ethane, ethanol, ethyl ether and by-products containing three or more carbon atoms from said reactor 28 with the cooling water 14 to obtain a quenched ethylene stream 15 at the top of said quenching column 31 and organic wastewater 16 including ethane, ethanol, ethyl ether and by-products containing three or more carbon atoms at the bottom of said quenching column 31, wherein the quenched ethylene stream 15 is fed to said first separation column 24;

a fourth separation column 32, connected to the bottom of said quenching column 31, used for receiving and separating the organic wastewater 16 including ethane, ethanol, ethyl ether and by-products containing three or more carbon atoms from the bottom of said quenching column 31 to obtain a water stream 17 at the bottom of said fourth separation column 32 and a fourth light components 19 including ethane, ethanol, ethyl ether and by-products containing three or more carbon atoms at the top of said fourth separation column 32;

a third condenser 33, connected to the top of said fourth separation column 32, used for receiving and condensing a fourth light components 19 from the top of said fourth separation column 32 to obtain a third condensate 20; and a second reflux tank 34, connected to said third condenser 33 and said fourth separation column 32 respectively, used for receiving a third condensate 20 from said third condenser 33, wherein a first part 21 of said third condensate is returned to the upper part of said fourth separation column 32, and a second part 22 of said third condensate and a second vapor-phase stream 23 produced therein are exhausted.

EXAMPLE 4

An ethylene stream 1 including ethane, ethanol, ethyl ether and by-products containing three or more carbon atoms from said reactor 28 enters into the first separation column 24 to be separated, thereby a first light components 3 containing ethylene being obtained at a top of said first separation column 24 and a first heavy components 2 containing ethylene being obtained at a bottom of said first separation column 24.

The volume of flow of each of the components of said ethylene stream 1 including ethane, ethanol, ethyl ether and by-products containing three or more carbon atoms is: hydrogen 0.070 kg/h, methane 0.070 kg/h, carbon monoxide 0.557 kg/h, ethylene 1274.518 kg/h, ethane 7.060 kg/h, propane 1.555 kg/h, acetaldehyde 0.113 kg/h, ethyl ether 5.631 kg/h, the heavy components 33.957 kg/h.

The volume of flow of the first heavy components 2 obtained at the bottom of the first separation column 24 is 83.866 kg/h, wherein the volume of flow of ethylene is 18.593 kg/h. The volume of flow of the first light components 3 obtained at the top of the first separation column 24 is 4712.040 kg/h, wherein the volume of flow of ethylene is 4709.413 kg/h. The light components 3 is condensed by the first condenser 25, and the first condensate is obtained, wherein the volume of flow of the first part 6 of the first condensate returned to the first separation column 24 is 3438.507 kg/h, the volume of flow of the second part 7 of the first condensate serving as the feedstock of the third separation column 26 is 1273.520 kg/h, and the volume of flow of the exhausted light components is zero. The temperature of the top of the first separation column 24 is −25.0° C., the pressure therein is 2.15 MPaG, the temperature of the bottom of the first separation column 24 is 9.3° C., the theoretical plate number of the whole column is 80, and the feed location is in the lower part of the first separation column 24. The heat load of the first condenser 25 is 434.501 kw.

The first heavy components 2 obtained at the bottom of the first separation column 24 are pumped to the top of the second separation column 27 to be separated. The temperature of the top of the second separation column 27 is 9.6° C., the pressure therein is 2.16 MPaG, the temperature of the bottom of the second separation column 27 is 59° C., the theoretical plate number of the whole column is 12. After being separated by the second separation column 27, the materials mainly containing ethylene steamed from the top of the second separation column 27 are returned to the bottom of the first separation column 24, and the volume of flow thereof is 33.866 kg/h; the second heavy components 11 mainly comprising ethane and other mixtures containing three or more carbon atoms (C3+) are exhausted from the bottom of the second separation column 27, the volume of flow thereof is 50.102 kg/h, and the volume of flow of ethylene is 1.696 kg/h. The heat load of the reboiler of the second separation column 27 is 4.691 kw.

The temperature of the top of the third separation column 26 is −22.7° C., the pressure therein is 2.35 MPaG, the temperature of the bottom of the third separation column 26 is −21.6° C., the theoretical plate number of the whole column is 18, and the feed location is in the upper part of the first separation column 26. After being separated, the third light components 8 containing ethylene steamed from the top of the third separation column 26 are partially condensed by the second condenser 29, whereby the vapor-phase components and liquid-phase components are separated, and the second condensate 10 and the first vapor-phase stream 9 are obtained. The second condensate 10 is returned to the third separation column 26, the first vapor-phase stream 9 is exhausted, and the volume of flow thereof is 7.815 kg/h, wherein the volume of flow of ethylene is 7.133 kg/h. The refined ethylene product is obtained at the bottom of the third separation column 26, the volume of flow thereof is 1265.638 kg/h, and the purity of ethylene reaches 99.998%.

The heat load of the second condenser 29 of the third separation column 26 is 29.141 kw, and the heat load of the reboiler thereof is 41.149 kw.

The yield of ethylene produced by the present separation technology is 99.30% (by weight).

EXAMPLE 5

As shown in FIG. 3, the volume of flow of the ethanol stream 12, with the purity of 99.60% (by weight), is 2312.5 kg/h. Under the conditions of the reaction temperature being 350° C. and the operating pressure being 0.8 MPaG, the vapor-phase components enter into the reactor 28 and contact with the catalyst, i.e., $\gamma$-$Al_2O_3$, whereby the vapor-phase components are dehydrated and the ethylene stream 1 including ethane, ethanol, ethyl ether and by-products containing three or more carbon atoms is obtained. The ethylene stream 1 including ethane, ethanol, ethyl ether and by-products containing three or more carbon atoms enters into the bottom of the quenching column 31 and countercurrent contact with the cooling water 14 entered from the top of the quenching column 31, and the quenched ethylene stream 15 and the organic wastewater 16 are obtained at the top of the quenching column 31. The organic wastewater 16, containing 0.242% (by weight) ethanol, enters into the upper part of the fourth separation column 32. The fourth light components 19 containing high concentration of ethanol separated from the top of the fourth separation column 32 enter into the second reflux tank 34 after being condensed by the third condenser 33, whereby the second vapor-phase stream 23 is separated and exhausted, and the third condensate 20 is separated. The first part 21 of the third condensate 20 is returned to the fourth separation column 32, the second part 22 of the third condensate 20, containing 73.37% ethanol (by weight) and the volume of flow thereof being 30.22 kg/h, is returned to the dehydration reaction system. The water stream 17, separated from the bottom of the fourth separation column 32, with the volume of flow thereof being 9200.64 kg/h and the content of organic substances being less than or equal to 20 ppm, is exhaust.

The temperature of the top of the fourth separation column 32 is 100.3° C., the pressure therein is 0.11 MPaG, the temperature of the bottom of the fourth separation column 32 is 123.3° C., the theoretical plate number of the whole column is 21. The heat source is provided to the fourth separation column 32 by means of reboiler way, and the heat load thereof is 857.32 kw.

The quenched ethylene stream 15, after the treatments of removing $CO_2$, being compressed and dehydrated, enters into the first separation column 24. The first light components 3 containing ethylene separated from the top of the first separation column 24 is condensed by the first condenser 25, and the first condensate is obtained. The first part 6 of the first condensate is returned to the first separation column 24, and the second part 7 of the first condensate enters into the middle part of the third separation part 26. The first heavy components 2 containing ethylene separated from the bottom of the first separation column 24 enter into the upper part of the second separation column 27. After separation of the second separation column 27, the second light components 4 mainly containing ethylene are steamed from the top of the second separation column 27 and are returned to the lower part of the first separation column 24, and the volume of flow thereof is 45.0 kg/h; the second heavy components 11 mainly comprising ethane and other mixtures containing three or more carbon atoms are exhausted from the bottom of the second separation column 27, the volume of flow thereof is 50.0 kg/h, and the volume of flow of ethylene is 0.87 kg/h.

The temperature of the top of the second separation column 27 is 6.3° C., the pressure therein is 2.16 MPaG, the temperature of the bottom of the second separation column 27 is 64.4° C., the theoretical plate number of the whole column is 11. The heat load of the reboiler is 6.04 kw.

The second part 7 of the first condensate enters into the middle part of the third separation column 26. The third light components 8 containing ethylene steamed from the top of the third separation column 26 are condensed by the second condenser 29 and separated by the first reflux tank 30, whereby the vapor-phase components and liquid-phase components are separated, and the first vapor-phase stream 9 is obtained and exhausted, and the volume of flow thereof is 7.95 kg/h, in which the volume of flow of ethylene is 7.25 kg/h. The refined ethylene product is obtained at the bottom of the third separation column 26, the volume of flow thereof is 1279.40 kg/h, and the purity of ethylene reaches 99.998%.

The temperature of the top of the third separation column 26 is −22.7° C., the pressure therein is 2.35 MPaG, and the temperature of the bottom of the third separation column 26 is −21.6° C. The heat load of the second condenser 29 is 29.50 kw, and the heat load of the reboiler of the third separation column 26 is 41.15 kw.

The invention claimed is:

1. An apparatus for producing ethylene, comprising:
   a reactor, configured for dehydrating ethanol and obtaining an ethylene stream including ethane, ethanol, ethyl ether and by-products containing three or more carbon atoms;
   a first separation column, connected to said reactor, configured for separating said ethylene stream including ethane, ethanol, ethyl ether and by-products containing three or more carbon atoms from said reactor to obtain a first light components containing ethylene at the top of said first separation column and a first heavy components containing ethylene at the bottom of said first separation column;
   a second separation column, the upper part of said second separation column being connected to the bottom of said first separation column, the top of said second separation column being connected to a lower part of said first separation column, said second separation column configured for receiving and separating the first heavy components containing ethylene from the bottom of said first separation column to obtain a second light components containing ethylene at the top of said second separation column and a second heavy components at the bottom of said second separation column, wherein the second light components are returned to the lower part of said first separation column and the second heavy components are exhausted;
   a first condenser, an inlet of said first condenser being connected to the top of said first separation column, and an outlet of said first condenser being connected to an upper part of said first separation column, said first condenser configured for condensing the first light components containing ethylene from the top of said first separation column to obtain a first condensate, wherein a first part of said first condensate is returned to the upper part of said first separation column; and
   a third separation column, configured for receiving and separating a second part of said first condensate from said first condenser to obtain a liquid ethylene at the bottom of said third separation column and a third light components at the top of said third separation column.

2. The apparatus according to claim 1, wherein said apparatus further comprises:
a second condenser, connected to the top of said third separation column, configured for receiving and condensing the third light components from the top of said third separation column to obtain a second condensate; and
a first reflux tank, connected to said second condenser and said third separation column respectively, configured for receiving a second condensate from said second condenser and returning said second condensate to an upper part of said third separation column.

3. The apparatus according to claim 1 wherein said apparatus further comprises:
a quenching column, connected between said reactor and said first separation column, configured for receiving and water quenching the ethylene stream including ethane, ethanol, ethyl ether and by-products containing three or more carbon atoms from said reactor to obtain a quenched ethylene stream at the top of said quenching column and organic wastewater including ethane, ethanol, ethyl ether and by-products containing three or more carbon atoms at the bottom of said quenching column, wherein the quenched ethylene stream is fed to said first separation column; and
a fourth separation column, connected to the bottom of said quenching column, for receiving and separating the organic wastewater including ethane, ethanol, ethyl ether and by-products containing three or more carbon atoms from the bottom of said quenching column to obtain a water stream at the bottom of said fourth separation column and a fourth light components including ethane, ethanol, ethyl ether and by-products containing three or more carbon atoms at the top of said fourth separation column.

4. The apparatus according to claim 3, wherein said apparatus further comprises:
a third condenser, connected to the top of said fourth separation column, for receiving and condensing a fourth light components from the top of said fourth separation column to obtain a third condensate; and
a second reflux tank, connected to said third condenser and said fourth separation column respectively, configured for receiving a third condensate from said second condenser, wherein a first part of said third condensate is returned to an upper part of said fourth separation column, and a second part of said third condensate is exhausted.

5. The apparatus according to claim 1 wherein an operating temperature of said first separation column ranges from −35° C. to 30° C., an operating pressure thereof ranges from 1.3 MPaG to 4.5 MPaG, and a theoretical plate number thereof ranges from 50 to 140.

6. The apparatus according to claim 1 wherein an operating temperature of said second separation column ranges from −15° C. to 80° C., an operating pressure thereof ranges from 1.0 MPaG to 4.0 MPaG, and a theoretical plate number thereof ranges from 2 to 50.

7. The apparatus according to claim 1 wherein an operating temperature of said third separation column ranges from −45° C. to −10° C., an operating pressure thereof ranges from 1.2 MPaG to 4.3 MPaG, and a theoretical plate number thereof ranges from 2 to 60.

8. The apparatus according to claim 1 wherein an operating temperature of said third separation column ranges from 30° C. to 210° C., an operating pressure thereof ranges from 0 MPaG to 1.0 MPaG, and a theoretical plate number thereof ranges from 2 to 98.

9. A method for producing ethylene using the apparatus according to claim 1, comprising:
1) feeding ethanol to the reactor to dehydrate said ethanol to obtain an ethylene stream including ethane, ethanol, ethyl ether and by-products containing three or more carbon atoms;
2) feeding said ethylene stream including ethane, ethanol, ethyl ether and by-products containing three or more carbon atoms obtained in step 1) to said first separation column and separating the ethylene stream to obtain a first light components containing ethylene at the top of said first separation column and a first heavy components containing ethylene at the bottom of said first separation column;
3) feeding the first heavy components containing ethylene obtained in step 2) to an upper part of said second separation column, and separating the first heavy components in said second separation column to obtain a second light components containing ethylene at the top of said second separation column and a second heavy components at the bottom of said second separation column, wherein the second light components are returned to the lower part of said first separation column and the second heavy components are exhausted; at the same time, feeding the first light components containing ethylene obtained in step 2) to said first condenser to obtain a first condensate, wherein the first part of the first condensate is returned to the upper part of said first separation column; and
4) feeding the second part of said first condensate to a third separation column to obtain a liquid ethylene at the bottom of said third separation column and a third light components at the top of said third separation column.

10. The method according to claim 9, wherein said method further comprises:
5) feeding said third light components obtained in step 4) to a second condenser to obtain a second condensate; and
6) feeding said second condensate obtained in step 5) to a first reflux tank, and then the second condensate is returned to an upper part of said third separation column through said first reflux tank.

11. The method according to claim 9 wherein said method further comprises:
before feeding the ethylene stream including ethane, ethanol, ethyl ether and by-products containing three or more carbon atoms obtained in step 1) to said first separation column in step 2), feeding aforementioned ethylene stream to a quenching column first and water quenching aforementioned ethylene stream, and then feeding the quenched ethylene stream obtained at the top of said quenching column to said first separation column to obtain an organic wastewater including ethane, ethanol, ethyl ether and by-products containing three or more carbon atoms at the bottom of said quenching column; the organic wastewater is then fed to a fourth separation column to obtain a water stream with organic contents less than 20 ppm by volume at the bottom of said fourth separation column and a fourth light components including ethane, ethanol, ethyl ether and by-products containing three or more carbon atoms at the top of said fourth separation column.

12. The method according to claim 11, wherein said method further comprises:

feeding the fourth light components to a third condenser to obtain a third condensate; and then the third condensate is fed to a second reflux tank, wherein a first part of said third condensate is returned to the upper part of said fourth separation column through said second reflux tank and a second part of said third condensate is exhausted.

13. The method according to claim 9, wherein an operating temperature of said first separation column ranges from −35° C. to 30° C., an operating pressure thereof ranges from 1.3 MPaG to 4.5 MPaG, and a theoretical plate number thereof ranges from 50 to 140.

14. The method according to claim 9, wherein an operating temperature of said second separation column ranges from −15° C. to 80° C., an operating pressure thereof ranges from 1.0 MPaG to 4.0 MPaG, and a theoretical plate number thereof ranges from 2 to 50.

15. The method according to claim 9, wherein an operating temperature of said third separation column ranges from −45° C. to −10° C., an operating pressure thereof ranges from 1.2 MPaG to 4.3 MPaG, and a theoretical plate number thereof ranges from 2 to 60.

16. The method according to claim 9, wherein an operating temperature of said third separation column ranges from 30° C. to 210° C., an operating pressure thereof ranges from 0 MPaG to 1.0 MPaG, and a theoretical plate number thereof ranges from 2 to 98.

17. The method according to claim 9, wherein a weight ratio of the first part of said first condensate and the second part of said first condensate ranges from 1 to 6:1.

18. The method according to claim 12, wherein a weight ratio of the first part of said third condensate and the second part of said third condensate ranges from 0.1 to 6:1.

19. The apparatus according to claim 2, wherein said apparatus further comprises:

a quenching column, connected between said reactor and said first separation column, used for receiving and water quenching the ethylene stream including ethane, ethanol, ethyl ether and by-products containing three or more carbon atoms from said reactor to obtain a quenched ethylene stream at the top of said quenching column and organic wastewater including ethane, ethanol, ethyl ether and by-products containing three or more carbon atoms at the bottom of said quenching column, wherein the quenched ethylene stream is fed to said first separation column; and a fourth separation column, connected to the bottom of said quenching column, for receiving and separating the organic wastewater including ethane, ethanol, ethyl ether and by-products containing three or more carbon atoms from the bottom of said quenching column to obtain a water stream at the bottom of said fourth separation column and a fourth light components including ethane, ethanol, ethyl ether and by-products containing three or more carbon atoms at the top of said fourth separation column.

20. The method according to claim 10, wherein said method further comprises:

before feeding the ethylene stream including ethane, ethanol, ethyl ether and by-products containing three or more carbon atoms obtained in step 1) to said first separation column in step 2), feeding aforementioned ethylene stream to a quenching column first and water quenching aforementioned ethylene stream, and then feeding the quenched ethylene stream obtained at the top of said quenching column to said first separation column to obtain an organic wastewater including ethane, ethanol, ethyl ether and by-products containing three or more carbon atoms at the bottom of said quenching column; the organic wastewater is then fed to a fourth separation column to obtain a water stream with organic contents less than 20 ppm by volume at the bottom of said fourth separation column and a fourth light components including ethane, ethanol, ethyl ether and by-products containing three or more carbon atoms at the top of said fourth separation column.

* * * * *